United States Patent [19]
Sitoto

[11] Patent Number: 6,074,393
[45] Date of Patent: *Jun. 13, 2000

[54] BONE FIXING SCREWS

[75] Inventor: Hideo Sitoto, Tokyo, Japan

[73] Assignee: Robert Reid, Inc., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/868,504

[22] Filed: Jun. 4, 1997

[30]  Foreign Application Priority Data

Jun. 7, 1996 [JP] Japan ................................ 8-006136
Aug. 29, 1996 [JP] Japan ................................ 8-247170

[51] Int. Cl.[7] ...................................................... A61B 17/86
[52] U.S. Cl. ................................................. 606/73; 606/61
[58] Field of Search ........................... 606/60, 61, 72, 606/73, 75

[56]  References Cited

U.S. PATENT DOCUMENTS 5,067,955  11/1991  Cotrel ........................................ 606/61
5,603,714   2/1997  Kaneda et al. ............................ 606/61

*Primary Examiner*—Michael Buiz
*Assistant Examiner*—David O. Reip
*Attorney, Agent, or Firm*—Wolf, Greenfield & Sacks, P.C.

[57]  ABSTRACT

To allow for greater ease of rod installation in a bone fixing screw having a threaded portion, and to prevent an installed rod from slipping out of place, there is formed at an outer end of a thread 11, a rod-receiving portion 12 having an opening obliquely placed with respect to the axial direction of the thread 11, so that a rod 20 can be inserted in a slantwise direction, and when it is stored in the rod-receiving portion 12, the rod 20 is secured in place with a retaining screw 14.

3 Claims, 4 Drawing Sheets

BONE FIXING SCREWS

BACKGROUND OF THE INVENTION

The present invention relates to bone-fixing screws comprising a thread adapted to be screwed into a bone, and a fixing means located at the end thereof which is designed for installing rods into the screw.

In order to maintain bones in a specified orientation relationship, there are various known techniques for screwing a bone-fixing screw (as an implant) into bones in various parts of the body, such as the spine, and combining rods with said implanted screw so that the rods will be positioned alongside the bones. The screws of prior art are provided with a rod-fixing means. The rod-fixing means have an opening that is located either parallel to the axial direction of thread or on the side thereof, but both solutions have their own problems; inserted rods slipped out of place easily with the former parallel arrangement, while with the latter, operators had to insert a rod at right angles to the axis of the thread, which proved to be a difficult procedure.

SUMMARY OF THE INVENTION

The bone-fixing screw of the present invention has been developed in view of the prior art described above, (including the drawbacks of the prior art bone-fixing means,) and it is accordingly an object of the present invention to provide a bone-fixing means adapted to ensure that rods will be easier to install and will prevent the installed rods from moving out of the opening. This and other objects have been attained by the bone-fixing screws which comprises a bone-fixing screw having a rod-receiving portion formed at the outer end of a thread, said rod-receiving portion having an oblique opening located with reference to the axial direction of the thread so that rods can be inserted slantwise, and a retaining screw for securing the rod in said rod-receiving portion.

DETAILED DESCRIPTION OF PREFERRED EMBODIMENTS

Figure 1:
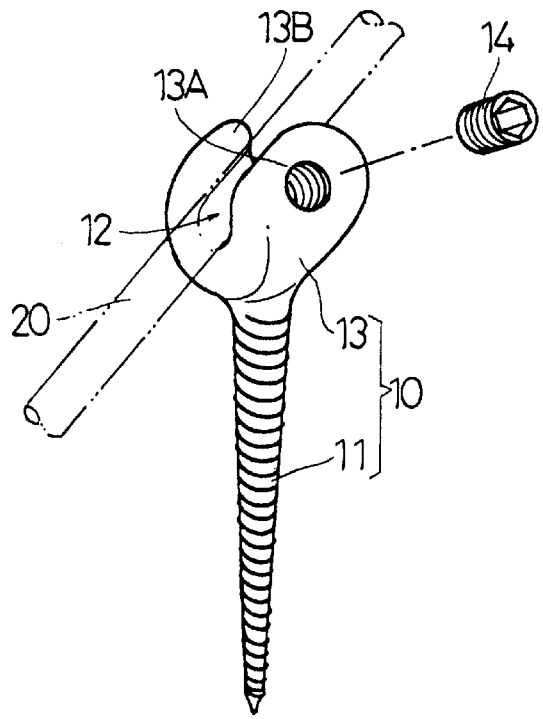
FIG. 1 is a perspective view of one embodiment of a screw for fixing bones according to the present invention.
Figure 2:
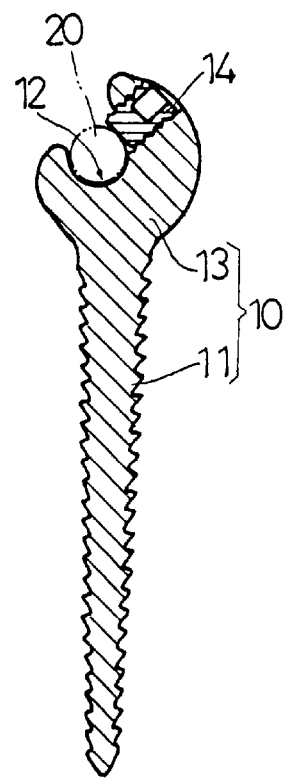
FIG. 2 is a longitudinal sectional view of the above.

A screw 10 of the present invention consists of a thread 11 adapted to be screwed into the bone V of the vertabra of the spine or neck bone, and an enlarged head 13 located at the outer end of said screw 10 and having a means for fixing a rod 20.

As the name denotes, the thread 11 is a male screw thread that serves as a means for implanting the screw 10 of the present invention. The length of threads 11 may be varied to provide screws 10 in a plurality of forms.

Figure 3:
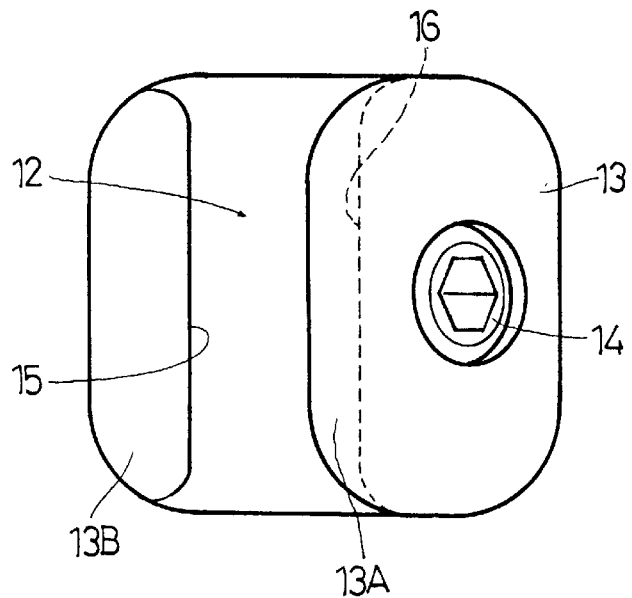
FIG. 3 is an enlarged plan view of the major portion of the above.
Figure 4:
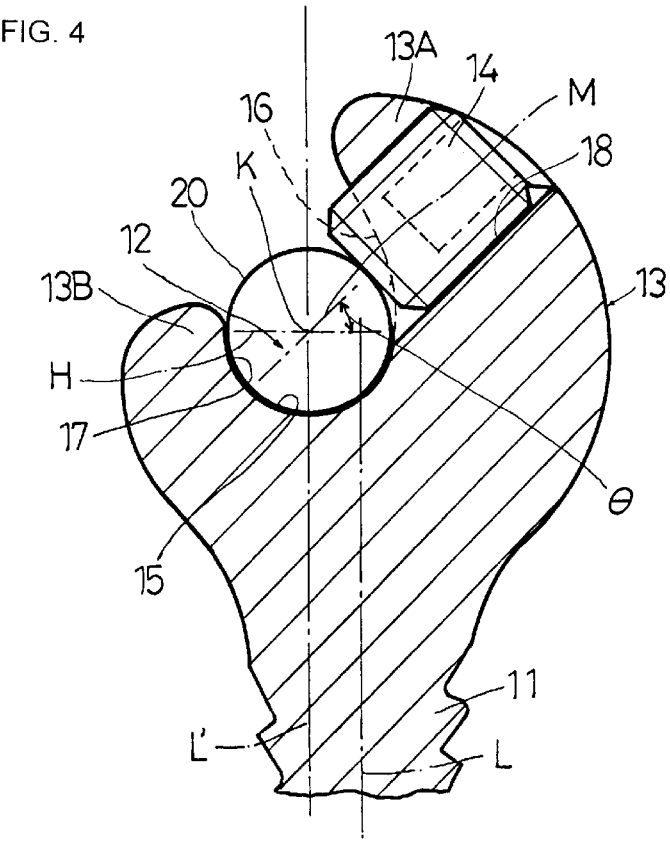
FIG. 4 is an enlarged sectional view.

At the outer end of said thread 11, there is formed a rod-receiving portion 12 having an opening placed angularly with respect to the axial direction thereof so that a rod 20 can be inserted obliquely. The example shown in FIG. 4 is so constructed that the rod-receiving portion 12 is located on an axis L', which is offset from an axis L of the thread 11 in parallel therewith, and a center axis K of the rod 20 is on the offset axis L'. The rod-receiving portion 12 takes the form of a groove having a concave cylindrical surface 15 that runs parallel to the rod 20 (see FIGS. 3 and 4), and, accordingly, the direction of the rod 20 is defined by that of the concave cylindrical surface 15.

The opening of the rod-receiving portion 12 is formed obliquely with reference to the axis L, thus permitting the rod 20 to be inserted in a slantwise direction. This results in increased ease when mounting rods, and prevents the rod from shifting upwards (outwardly away from the axial direction) out of the opening. This "gangled" formation of the rod-receiving portion 12 brings it into a state where it is surrounded by a longer arm 13A extending toward the axial direction and a shorter arm 13B.

This arrangement produces an overhang 16 inside the longer arm 13A of the rod-receiving portion 12 which the rod 20 contacts when it starts to shift away from the axial direction. The inside of the shorter arm 13B of the rod-receiving portion 12 serves as a stopper 17 that prevents the rod from slipping laterally out of the rod-receiving portion. More concretely, the shorter arm 13B extends slightly above the horizontal line H running through the center axis K of the rod 20 when it is stored in the rod-receiving portion 12, thus securely holding the rod 20.

The rod 20 thus fitted into the rod-receiving portion 12 is secured to the screw 10 with a retaining screw 14. Another way of saying this is that the rod 20 can be retained there because it is secured to the screw 10 with the retaining screw 14. The retaining screw 14 is screwed into a female screw thread hole 18 formed in a head 13 of the screw. The female screw thread hole 18 shown, which is provided in the longer arm 13A of the head 13, is opposed to the center axis K of the rod 20 in the rod-receiving portion 12.

Part of the force exerted to clamp the rod 20 with the retaining screw 14 acts on the shorter arm 13B, and the remainder on the longer arm 13A. In view of the foregoing, the shorter arm 13B was constructed to have a thin wall due to its small moment arm, and the longer arm 13A was constructed to have a thick wall because of its longer moment arm. Each arm is thus imparted with the strength sufficient and necessary to ensure that it can fix the rod accurately by tightening the retaining screw 14 to the maximum torque without causing any deflection of the head 13.

In this embodiment, an angle θ formed between the axial line M of the female screw thread hole 18 and the horizontal line H running through said center axis K was specified at 45° to 65°. It was thereby proven that a rod 20 could be set advantageously into a rod-receiving portion 12 through a narrow cut opening during a surgical operation. The angle θ can be any angle between 40° and 70°, but preferably, it should be between 45° and 65°. If the angle θ is smaller than 40°, the rod 20 will be apt to slip out, and if it exceeds 70°, the opening will stand substantially upright, thereby resulting in a loss of the advantages of the angular formation of the opening.

Figure 7:
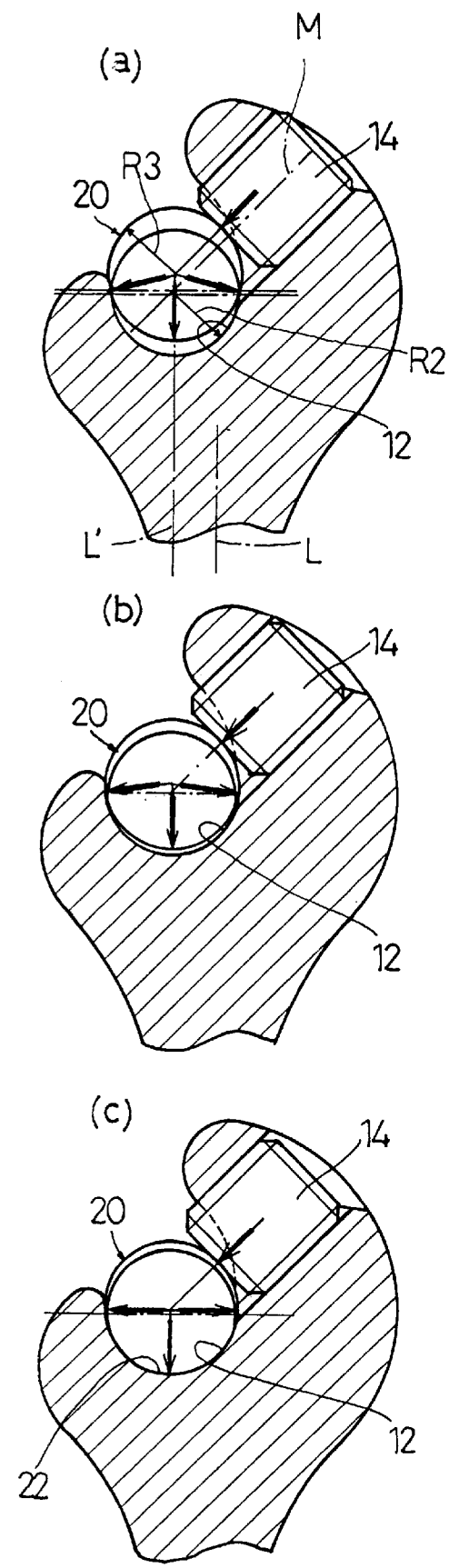
FIG. 7(a) is a sectional view indicating the state of a rod immediately after it starts to receive pressure from a retaining screw.
FIG. 7(b) is a sectional view indicating the state in which a rod-receiving portion is advancing into a rod.
FIG. 7(c) is a sectional view indicating the state in which a rod has been completely fitted into the rod-receiving portion.

If a radius R2 of the rod-receiving portion 12 is specified to be a slightly smaller size than a radius R3 of the rod 20, the rod pushes its way into the rod-receiving portion 12, expanding the inside diameter thereof until it becomes equal to the radius R3 of the rod 20 (FIG. 7). In this example, the pressure applied by the retaining screw 14 is employed to insert the rod 20 into the rod-receiving portion 12, and after it is completely fitted in, it is subjected to pressure due to the elastic deformation of the rod-receiving portion 12.

The degree to which the inner diameter of the rod-receiving portion 12 is made smaller than the outside diameter of the rod should preferably be on the order of 40 percent of the maximum deflection of the rod-receiving portion 12. FIG. 7(a) indicates a state in which the rod 20, supported at the entrance of the rod-receiving portion 12, starts to receive pressure from the retaining screw 14. As the screw 14 is progressively tightened, the rod 20 proceeds inward, enlarging the diameter of the rod-receiving portion 12 (FIG. 7(b)), and the rod 20 goes further until it bears on an inner surface 22 thereof for stabilization (FIG. 7(c).)

In the example in FIG. 7 as well, the direction of the opening of the rod-receiving portion 12, as well as the direction of the axis line M along which the retaining screw 14 is screwed is identical to those in the examples shown in FIGS. 1 through 4. More specifically, the opening of the rod-receiving portion 12 is placed on the left side of the axis L, and the female thread hole 18 is on the right, both of which are directed to the center axis K.

Figure 5:
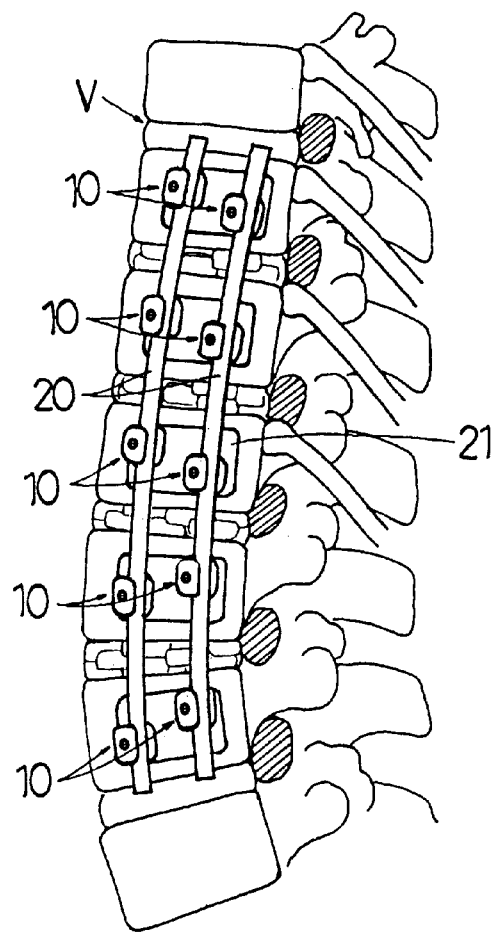
FIG. 5 is a side view depicting the state in which said embodiment is in actual use.
Figure 6:
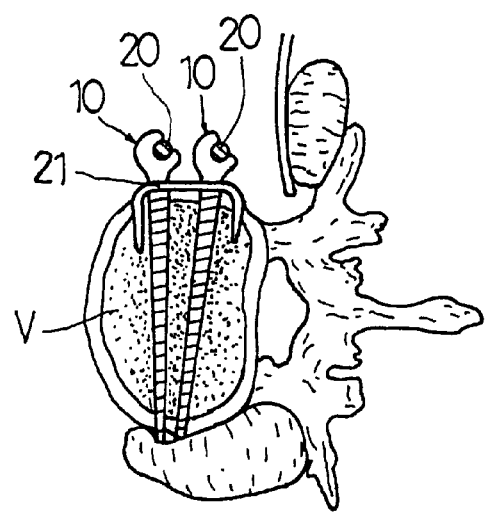
FIG. 6 is a horizontal sectional view of the above.

Thus constructed screw 10 functions in such a manner that the thread 11 thereof is screwed into the bone V to arrange a plurality of screws in a specified relationship, and the rod 20 is inserted into the rod-receiving portion 12 of each screw 10 to secure the assembly with the retaining screw 14 (see FIGS. 5 and 6). An object designated with the reference number 21 is a plate for vertebral body that can be fitted for use at the side of the vertebral body employed in the screws according to this invention, and also serves as a guide for installing a screw.

In the example shown in the figures attached, two rods 20 are employed, and although the rod-receiving portion 12 of each screw 10 faces in the same direction (to the right in the case of FIG. 5), the rod-receiving portions could be arranged so that they are opposed to each other.

The screw according to the present invention is so configured and operated as previously described that it enables the rod 20 to be inserted slantwise into the rod-receiving portion 12. This means that a smaller portion of human body is required to be exposed during a surgical operation than when a rod is inserted from the side. The screw of this invention can make it easier to mount a rod therein, and, at the same time, can make it much simpler to handle the rod because the angled arrangement of the rod-receiving portion 12 creates the overhang 16 that prevents the rod 20 from coming out of the rod-receiving portion.

The bone-fixing screw of the present invention offers the further advantage that the radius of the rod-receiving portion 12 is set to a dimension that is a little smaller than that of the rod 20, and it can be widened to the outside diameter of the rod 20 once it is fitted completely in the rod-receiving portion 12, thereby ensuring that the rod 20 can be secured in place. This also prevents the rod 20 from slipping out of place upon removal of the retaining screw 14.

What is claimed is:

1. A bone-fixing screw having a thread to be screwed into a bone and a fixing means located at an outer end thereof which comprises a rod-receiving portion and a retaining screw for installing rods, said rod-receiving portion being formed at the outer end of a threaded shaft and having an opening angularly placed with respect to an axial direction of said threaded shaft so that a rod can be inserted in a slantwise direction, and said retaining screw having an axis angularly arranged to said axial direction of said threaded shaft and being employed to secure a rod in said rod-receiving portion in a fixed position which maintains its position in use, said screw is so constructed that an enlarged head is disposed at the outer end of said threaded shaft and a rod-receiving portion composed of a cylindrical surface parallel to a rod 20 is grooved, said rod-receiving portion having an angular opening is surrounded by an axially extending long arm carrying said retaining screw and another arm that is shorter and thinner than the long arm to allow torque being applied by said retaining screw to reform said shorter arm and closely grip a rod inserted into said rod receiving portion without movement of said long arm.

2. A bone-fixing screw as claimed in claim 1, wherein a radius of said rod-receiving portion is slightly smaller than an adjacent radius of a rod so that an inside diameter of the rod-receiving portion is widened when a rod has been completely seated into said rod receiving portion until said inside diameter of said rod receiving portion is equal to an outside diameter of said rod, and said center of said rod is displaced from a center axis of said threaded shaft, and said rod receiving portion has a first arm and a second arm thinner than said first arm.

3. A bone fixing screw as claimed in claim 1 wherein:

a radius of said rod-receiving portion is slightly smaller than an adjacent radius of a rod, so that an inside diameter of the rod-receiving portion is widened when a rod has been completely seated into said rod receiving portion until said inside diameter of said rod receiving portion is equal to an outside diameter of said rod.

* * * * *